United States Patent [19]

Cutler et al.

[11] Patent Number: 4,619,269

[45] Date of Patent: Oct. 28, 1986

[54] APPARATUS AND METHOD FOR MONITORING RESPIRATORY GAS

[75] Inventors: Christopher A. Cutler, Bountiful; William D. Wallace, Salt Lake City, both of Utah

[73] Assignee: Utah Medical Products, Inc., Midvale, Utah

[21] Appl. No.: 599,080

[22] Filed: Apr. 11, 1984

Related U.S. Application Data

[63] Continuation-in-part of Ser. No. 509,209, Jun. 29, 1983, abandoned.

[51] Int. Cl.$^4$ .................. A61B 5/08; A61M 16/00
[52] U.S. Cl. .................. 128/719; 128/204.16; 128/205.23; 128/718
[58] Field of Search ........... 128/716, 719, 718, 204.21, 128/204.22, 204.15, 204.16, 205.12, 205.23; 55/158, 159; 62/3, 93, 272, 285

[56] References Cited

U.S. PATENT DOCUMENTS

| | | | |
|---|---|---|---|
| 2,792,828 | 5/1957 | Engelder | 128/2.07 |
| 3,507,146 | 4/1970 | Webb | 128/719 |
| 3,514,377 | 5/1970 | Spacil et al. | 204/1 |
| 3,592,191 | 7/1971 | Jackson | 128/204.16 |
| 3,895,630 | 7/1975 | Bachman | 128/719 |
| 4,075,481 | 2/1978 | Stoft et al. | 250/343 |
| 4,080,103 | 3/1978 | Bird | 128/204.16 |
| 4,211,239 | 7/1980 | Raemer et al. | 128/716 |
| 4,231,256 | 11/1980 | Chapman et al. | 62/3 |
| 4,233,842 | 11/1980 | Raemer et al. | 128/719 |
| 4,368,740 | 1/1983 | Binder | 128/718 |
| 4,430,192 | 2/1984 | Maeda | 204/410 |
| 4,440,177 | 4/1984 | Anderson et al. | 128/719 |

OTHER PUBLICATIONS

L. G. Wong et al., "Eliminating the Effect of Water Vapor in Respiratory Gas Analysis," 7, Journal of Clinical Engineering (No. 2), pp. 159–163 (Apr.–Jun. 1982).
A. C. Norton, "Development and Testing of a Microprocessor-Controlled System for Measurement of Gas Exchange and Related Variables in Man During Rest and Exercise," Beckman Reprint No. 025 (1982).
N. S. Deno et al., "A Dryer for Rapid Response On-Line Expired Gas Measurements," 46, J. Appl. Physiol.: Respirat. Environ. Exercise Physiol. (No. 6), pp. 1196–1199 (1979).
J. H. Willmore et al., "An Automated System for Assessing Metabolic and Respiratory Function During Exercise," 40, Journal of Applied Physiology (No. 4), pp. 619–624 (Apr. 1976).
J. H. Willmore et al., "Semiautomated Systems Approach to the Assessment of Oxygen Uptake During Exercise," 36, Journal of Applied Physiology (No. 5), pp. 618–620 (May 1974).
W. L. Beaver, "Water Vapor Corrections in Oxygen Consumption Calculations," 35, Journal of Applied Physiology (No. 6), pp. 928–931 (Dec. 1973).
K. Wasserman et al., "Anaerobic Threshold and Respiratory Gas Exchange During Exercise," 35, Journal of Applied Physiology (No. 2), pp. 236–243 (Aug. 1973).
J. H. Auchincloss, Jr. et al., "Control of Water Vapor During Rapid Analysis of Respiratory Gases in Expired Air," 28, Journal of Applied Physiology (No. 2), pp. 245–247 (Feb. 1970).
Advertisement of the Puritan-Bennett Corp., Kansas City, Missouri 64106, entitled "The $CO_2$ Monitoring System Features . . . ,".

*Primary Examiner*—Henry J. Recla
*Attorney, Agent, or Firm*—Workman, Nydegger & Jensen

[57] ABSTRACT

An apparatus and method for monitoring respiratory gases in newborn infants. The apparatus includes a first fluid flow circuit from which an oxygen enriched gas is used to ventilate the patient, and a second fluid flow circuit connected in parallel to the first circuit. The second fluid flow circuit is used to isolate respiratory gases expired by the infant so that the respiratory gases can be accurately monitored for concentrations of the carbon dioxide and oxygen, which are then used to calculate metabolic rate and other clinical data used in properly caring for the patient. The apparatus also includes electronic processing capability for quickly determining the needed data and for outputting it in a format which is convenient and readily available for use by doctors, nurses or technicians.

27 Claims, 5 Drawing Figures

APPARATUS AND METHOD FOR MONITORING RESPIRATORY GAS

RELATED APPLICATIONS

The present application is a continuation-in-part of application Ser. No. 509,209, filed June 29, 1983, now abandoned.

BACKGROUND

1. Field of the Invention

The present invention relates to metabolic gas monitoring apparatus and methods, and in particular, to a novel apparatus and method for measuring respiratory gases in newborn infants.

2. The Prior Art

Small newborn infants, particularly those born prematurely, often have insufficient lung development with the result that they suffer from respiratory distress. It has been found that vigorous mechanical ventilation of infants with various types of lung disorders significantly improves their expected rate of survival. However, one of the difficulties with mechanical ventilation of newborn infants is that it is extremely difficult to accurately monitor the ventilation. As a result of this problem it has been difficult to even decide how to properly set a mechanical ventilator so that adequate ventilation occurs without over or under ventilating the infant. Indeed, one of the dangers of mechanical ventilation has been the potential for hyperinflation of the infant's lungs, which may itself result in lung damage. Thus, to date rather cumbersome and inaccurate methods such as chest roentgenograms, arterial blood gas determinations and/or physical examination have been used in order to estimate whether the ventilator was set properly.

Apart from the decision of how to set the level of ventilation, analysis of the respiratory gas of a newborn infant is important for other reasons. By measuring the level of oxygen and carbon dioxide in the expired gas and comparing these levels with the levels of oxygen and carbon dioxide in the inspired gas, it is possible to determine metabolic rate using calculations which constitute a method known as indirect calorimetry. This information is highly useful in diagnosing various problems and also in developing an appropriate diet for the newborn infant. This information may be particularly important in the case of very premature or critically ill infants because improper nutrition at the early stages of life may cause permanent disorders and impede growth.

Accurate measurement of the respiratory gases of a newborn infant can also be used to estimate blood flow, which otherwise could only be roughly estimated using charts and tables, which is a much less accurate method. By carefully monitoring respiratory gases it is also possible to gain a good understanding of changes in cardiovascular function and tissue perfusion, which are also important considerations in clinically diagnosing and caring for newborn infants who may be critically ill.

In summary, it has long been recognized that accurate monitoring of respiratory gases would provide much information that would be highly useful to doctors, nurses and technicians caring for critically ill infants. However, to date the state of the art does not provide any apparatus or methods which are very satisfactory. Some attempts have been made to monitor respiratory gases in the case of infants which are well enough developed to breathe without the use of mechanical ventilation. In such cases the infant's head is typically placed under a hood into which an oxygen enriched gas is introduced. Attempts to monitor the respiratory gases of infants in this type of situation have typically used devices which evacuate the air from the hood. The difficulty with this procedure is that a newborn infant typically expires a relatively small volume of gas into the chamber of the hood, which is then mixed with the remaining gas in the hood before it is evacuated. Thus, this procedure is not very accurate.

Moreover, in the case of critically ill newborn infants mechanical ventilation must be used since typically these infants are incapable of breathing on their own. Especially in the case of a mechanically ventilated infant, the volume of gas expired by the infant is so small that it is extremely difficult to accurately monitor and detect the expired gases once they enter back into the ventilation stream. Thus, even though some attempts have been made in the prior art to place a monitoring apparatus into the ventilation stream downstream from the patient, such attempts have been largely unsuccessful in providing accurate measurement of the respiratory gases. Thus, to date there has not been devised a satisfactory apparatus or method for accurately monitoring the respiratory gases of newborn infants, especially in the case of those needing mechanical ventilation.

PRINCIPAL OBJECTS AND BRIEF SUMMARY OF THE INVENTION

In view of the prior state of the art, it is a principal object of the present invention to provide an apparatus and method which can be used to accurately monitor the respiratory gases of newborn infants, especially in the case of newborn infants requiring mechanical ventilation.

Another important object of the present invention is to provide an apparatus and method for monitoring respiratory gases of newborn infants which is simple to use and which quickly provides data from which the necessary information can be derived concerning the proper setting of the ventilator, the patient's metabolic rate, the patient's cardiovascular function and other important clinical data used to properly care for the patient.

Still another important object of the present invention is to provide an apparatus and method for monitoring respiratory gases of newborn infants which is relatively compact and inexpensive.

These and other objects and features of the present invention will become more fully apparent from the following description and appended claims, taken in conjunction with the accompanying drawings.

In the apparatus and method of the present invention, the foregoing principal objects are achieved by the use of a novel configuration for a respiratory gas monitoring circuit which is especially designed to isolate from the ventilation stream the gases expired by a newborn infant. Advantageously, this permits the gases expired by the infant to be very accurately monitored and analyzed for the purpose of developing data which can be used to determine the infant's metabolic rate, cardiovascular function and other important clinical data. The apparatus and method of the invention also include state of the art electronic processing capability for very quickly determining the needed data and for outputting it in a format which is convenient and readily available for use by doctors, nurses, technicians or others who need to evaluate and use the data. In addition, the present invention also incorporates a unique method and apparatus for removing water vapor from the expired gas stream.

BRIEF DESCRIPTION OF THE DRAWINGS

Reference is next made to a more detailed description of the presently preferred embodiment of the apparatus and method of the present invention with reference to the drawings, in which like parts are designated with like numerals throughout.

DETAILED DESCRIPTION OF THE PRESENTLY PREFERRED EMBODIMENT

Figure 1:
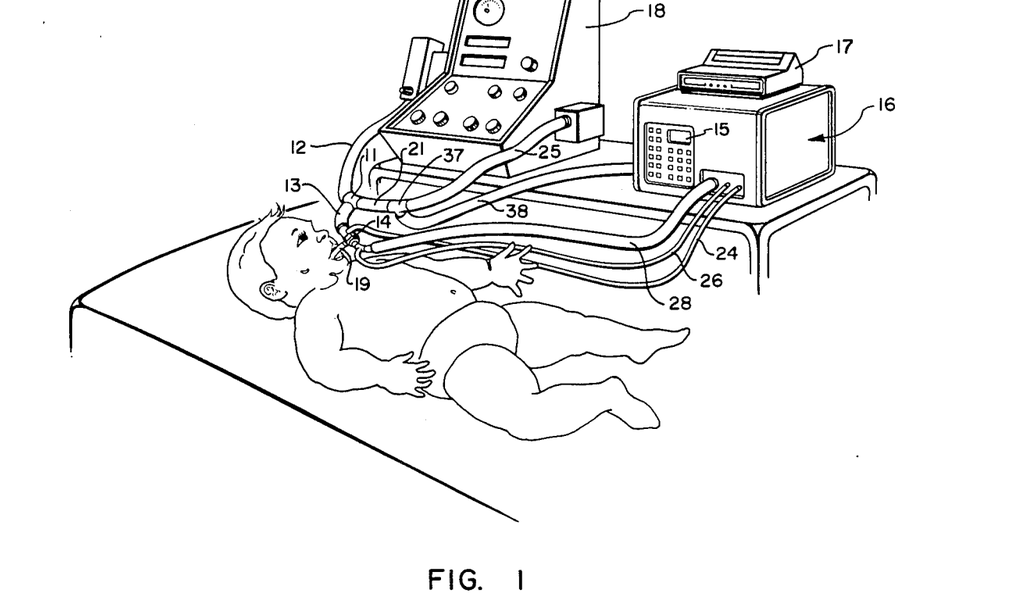
FIG. 1 is a perspective view of the apparatus and method of the present invention which generally illustrates the manner in which the apparatus may be used to monitor the respiratory gases in the case of a newborn infant requiring mechanical ventilation.

FIG. 1 is a perspective view which generally illustrates the manner in which the apparatus of the present invention would be used in the case of a newborn infant requiring mechanical ventilation. A conventional ventilator is illustrated at 18 and includes a ventilation tube 12 through which an oxygen enriched gas is provided to the infant. A "T" connector 11 is attached to the ventilation tube 12 and provides a connection to a short length of tubing 13 which leads to a small, two-way valve 14. The valve 14 in turn is attached to an endotracheal tube 19 which is inserted through the mouth of the infant into the trachea.

The two-way valve 14 permits the infant to inspire the oxygen enriched gas from the ventilation stream provided through tube 12. When the infant expires respiratory gas, the valve 14 closes at its inlet so that the expired gas is then forced through tube 28 which is connected to an electronically controlled metabolic gas monitor 16. Valve 14 may be any suitable type of two-way valve, such as a model no. 2300 valve manufactured by Hans Rudolph, Inc. of Kansas City, Mo. The size of valve may vary depending upon the size of the infant.

Connected at the outlet end of the two-way valve 14 is a small diameter tube 26 which can be used to sample endtidal gas for purposes of breath-by-breath analysis by the gas monitor 16, as hereinafter more fully described. A second small diameter tube 24 is connected upstream from the inlet of the two-way valve 14 so that inspired gas can be input through tube 24 to gas monitor 16.

The metabolic gas monitor 16 includes a digital display 15 and a printer 17 having graphics capability so that data concerning the infant's rate of metabolism or other clinical information can be conveniently displayed. As hereinafter more fully described, the metabolic gas monitor 16 is electronically controlled so that the data can be output quickly and accurately. After the respiratory gas has been analyzed by the metabolic gas monitor 16, it is returned through exhaust tube 38 which is connected by another "T" fitting 37 back into the main ventilation stream provided by tube 25.

As mentioned previously, in the case of mechanically ventilated infants one of the principal difficulties which has prevented accurate monitoring of respiratory gases arises from the fact that the volume of expired gas is very small in comparison to the volume and rate of gas flowing through the main ventilation stream. In the apparatus and methods used in the prior art, typically the infant is simply connected directly to the main ventilation stream through an endotracheal tube. Respiratory gases from the infant are thus typically expired back into the main ventilation stream, which makes it extremely difficult to accurately monitor the respiratory gases. The apparatus and method of the present invention overcomes this problem through the use of a novel configuration for a respiratory gas monitoring circuit which isolates the respiratory gases from the background flow in the main ventilation stream.

Figure 2:
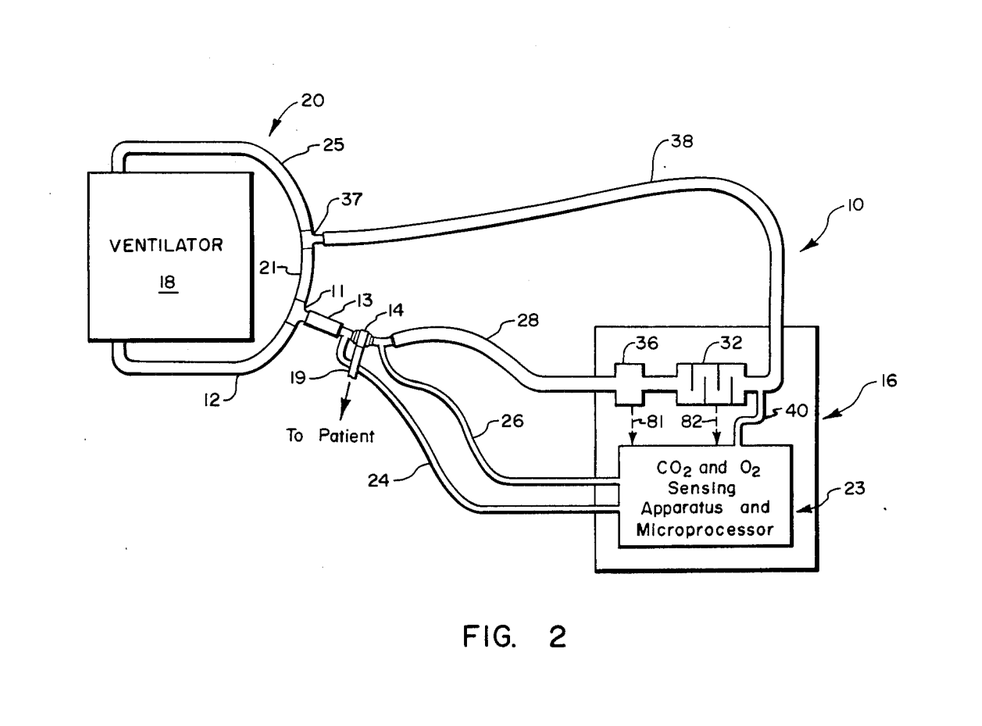
FIG. 2 is a simplified schematic diagram which generally illustrates a respiratory gas monitoring circuit which is used to isolate expired gas from the ventilation stream.

As shown best in FIG. 2, the expired respiratory gases flow through a circuit generally designated 10 which is separate from the main ventilation stream. The main ventilation stream flows through the circuit generally designated 20, which is comprised of two lengths of tubing 12 and 25 which are interconnected by another short length of tubing 21. At the point of interconnection between the lengths of tubing 12 and 21 there is a "T" fitting 11 which provides a connection through another short length of tubing 13 to the two-way valve 14 described above. The circuit 10 is comprised of the tubing 13, the two-way valve 14, a length of tubing 28 which is connected in series to a flow meter 36 and a mixing chamber 32, and another length of tubing 38 which is connected from the outlet of mixing chamber 32 back to the main ventilation stream by way of a "T" fitting 37.

Importantly, the resistance to fluid flow provided by the short length of tubing 21 is designed so that it is much less than the resistance to fluid flow provided through circuit 10. The resistance of circuit 10 consists of the resistance provided by each of the lengths of tubing 13, 28 and 38, added to the resistance provided by the two-way valve 14, the flow meter 36 and the mixing chamber 32. Preferably the components which form the circuit 10 (i.e., the lengths of tubing, two-way valve 14, flow meter 36 and mixing chamber 32) are selected such that the overall resistance to fluid flow through circuit 10 will be on the order of 10 to 100 times greater than the resistance to fluid flow through the short connecting length of tubing 21 through which the main ventilation stream passes.

The increased resistance of circuit 10 will prevent background flow from the main ventilation stream from passing completely through valve 14 and out tube 28 when the infant inspires, thus effectively isolating all expired respiratory gas from the main ventilation stream. The expired respiratory gases which are thus isolated from the main ventilation stream can then be sampled either through tube 40 or tube 26 and accurately analyzed by the $CO_2$ and $O_2$ sensing apparatus and electronic microprocessor, which are generally designated at 23 in FIG. 2. Inspired gases are sampled through a small tube 24 connected at the inlet end of valve 14.

Figure 3:
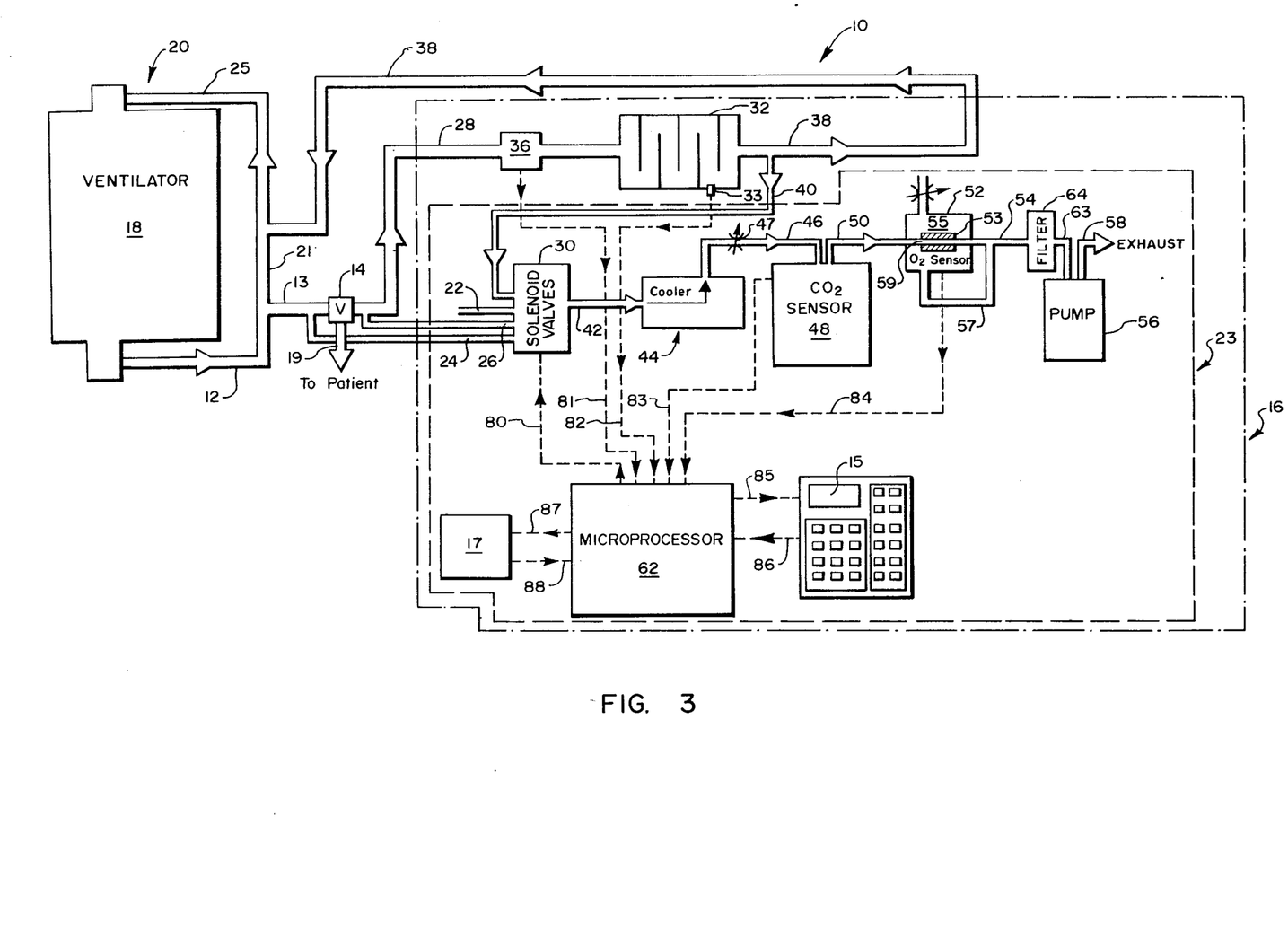
FIG. 3 is a schematic diagram which illustrates in greater detail the apparatus and method used to monitor and analyze the content of respiratory gases.
Figure 4:
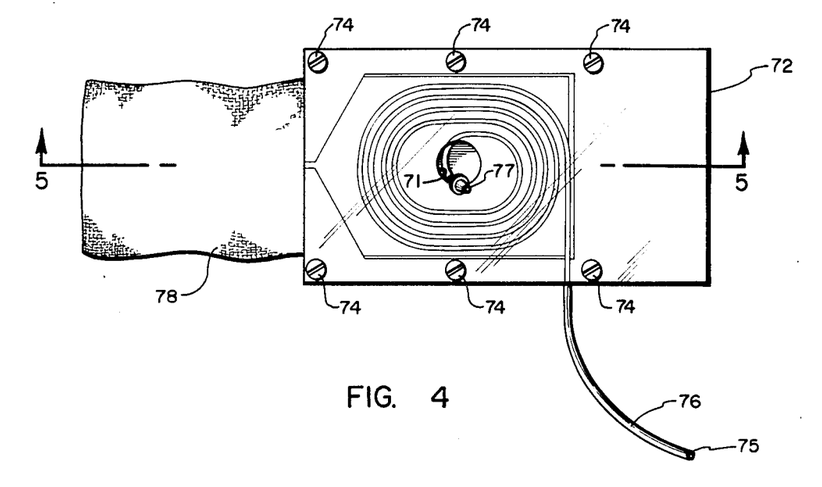
FIG. 4 is a vertical cross-sectional view of one of the components of the apparatus of FIG. 3 which is used to remove water vapor from the gas sample before it is tested for concentrations of carbon dioxide or oxygen.
Figure 5:
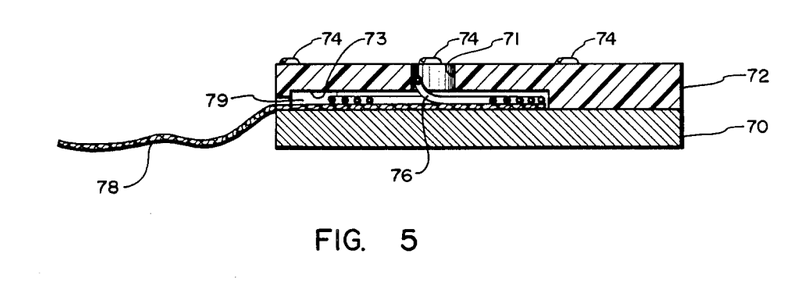
FIG. 5 is a horizontal cross-sectional view of the component shown in FIG. 4.

Reference is next made to FIGS. 3, 4 and 5 which illustrate in greater detail one presently preferred embodiment for implementing the apparatus and method of the present invention as generally illustrated in FIG. 2. It should be appreciated that the more detailed description in connection with FIG. 3 is intended to be merely illustrative of one example of how to make and use the apparatus and method of the present invention, and is not intended to be restrictive in terms of the scope of the invention.

As shown in FIG. 3, that portion of the apparatus which corresponds to the $CO_2$ and $O_2$ sensing apparatus and microprocessor generally designated at 23 in FIG. 2 is outlined by the dashed lines indicated at 23. Included in the metabolic gas monitoring apparatus 16 is an electronically controlled switching mechanism 30 which consists of a series of solenoid-actuated valves (not shown). Separate solenoid valves of switching mechanism 30 are controlled by microprocessor 62 as schematically indicated by line 80 so as to control the flow of gaseous samples through one of the inlet conduits 22, 24, 26 or 40. As previously mentioned, conduit 24 is used to sample the inspired gas at the inlet side of valve 14, whereas conduit 26 is used to provide a breath-by-breath sample of expired respiratory gas at the outlet side of valve 14. Conduit 40 is connected at the outlet of mixing chamber 32 and provides a sample of expired respiratory gas averaged over a short period of time by means of the mixing chamber 32. Conduit 22 is connected to an external source of calibration gas (not shown). Thus, switching mechanism 30 provides for the alternate introduction of a gaseous sample from one of the conduits 22, 24, 26 or 40 through the switching mechanism 30 and into the conduit 42. Switching mechanism 30 may be any suitable conventional solenoid valve system which can be electronically controlled, such as the LIF series of solenoid valves manufactured by the Lee Company of Westbrook, Conn.

Gas conduit 42 provides for the introduction of the gaseous sample from one of gas inlet conduits 22, 24, 26, and 40 into a thermoelectric cooler 44. Cooler 44 is illustrated in greater detail in FIGS. 4 and 5. Preferably, cooler 44 has a thermoelectric block 70 constructed of an aluminum base with a thermoelectric element (not shown). Securely attached to the top of block 70 is a block of insulating material 72 such as acrylic. The aluminum base 70 and the insulating block 72 may be attached in any acceptable conventional manner such as by screws 74. As shown in FIGS. 4 and 5 a length of tubing 76 runs into the device, forms a coil, and runs back out of the device through a hole 71 formed in block 72. The inlet end 75 of tubing 76 is connected to the conduit 42 (see FIG. 3), while the outlet end 77 of tubing 76 is connected to conduit 46. The length of tubing 76 is selected to provide adequate distance so that the gaseous sample can be cooled sufficiently to accomplish removal of the water vapor, as described below.

The insulating block is notched as at 73 (see FIG. 5) so as to form a chamber 79 which contains the coiled tubing 76. Also positioned between the aluminum base 70 and the insulating block 72 is a water absorbent wick 78 which extends out of the device 44. The coil of tubing 76 rests between the aluminum base 70 and the insulating layer 72 and upon the water absorbent wick 78.

The tubing 76 is made of a highly hydrophilic material. Thus, as gases are passed through the tubing, the cool aluminum block causes the water vapor to condense. Water then passes through the walls of the tubing but the gaseous sample remains within the tubing. The condensed water vapor is absorbed by the wick 78. Since a temperature gradient is created as between the cool block 70 and the ambient air, the water tends to migrate along the wick 78. Thus, the absorbed water passes outside the aluminum block 70 and insulating block 72 and evaporates as it travels to the outside portion of the wick 78.

Referring again to FIG. 3, a conduit 46 provides for gaseous communication between tubing 76 of cooler 44 and a carbon dioxide sensor 48. Sensor 48 may be any suitable conventional carbon dioxide sensor; for example, the "Series V" carbon dioxide sensor manufactured by Sensors, Inc., of Saline, Mich., has been found to be suitable for purposes of the present invention. A needle valve 47 is mounted within conduit 46 so as to allow for the adjustment and control of the flow of gas passing through conduit 46.

Another conduit 50 provides for gaseous communication between carbon dioxide sensor 48 and an oxygen sensor 52. A conduit 54 provides for communication between oxygen sensor 52 and a filter 64, while a conduit 63 provides for communication between filter 64 and a pump 56. Pump 56 serves to draw the gaseous samples from conduit 54, through filter 64 and conduit 63, and into an exhaust conduit 58 after analysis, while filter 64 acts to filter out impurities to protect pump 56.

In one presently preferred embodiment, oxygen sensor 52 is comprised of a zirconium oxide ($ZrO_2$) tube 53 (shown in cross section) which acts as a differential electrode. A reference gas (typically room air) having a relatively constant oxygen concentration is introduced through a conduit 49 and into a reference chamber 55 of oxygen sensor 52. A variable restrictor or needle valve 51 controls the flow of the reference gas into the reference chamber. A conduit 57 provides for gaseous communication between reference chamber 55 and conduit 54. A sample chamber 59 within zirconium oxide tube 53 provides for passage of a gaseous sample through oxygen sensor 52, sample chamber 59 being in gaseous communication with conduits 50 and 54.

The oxygen sensor 52 operates by introducing the gaseous sample to be analyzed, whether the calibration gas from conduit 22, the inspired gas from conduit 24, or the expired respiratory gas from conduits 26 or 40 into chamber 59. The sample exits from chamber 59 into conduit 54. The reference gas enters conduit 49 into reference chamber 55, and exits the reference chamber 55 through conduit 57. The reference gas then joins the gaseous sample at conduit 54, and the combined gas is withdrawn by pump 56 through filter 64 and conduits 63 and 58. The voltage differential imposed on zirconium oxide differential electrode 53 during passage of the reference and sample gases through sensor 52 is measured, and this data is electronically signalled to the microprocessing unit 62 for calculation of the concentration of oxygen in the gaseous sample passing through sample chamber 59.

Since sample chamber 59 and reference chamber 55 are in gaseous communication with each other by virtue of conduits 54 and 57, the absolute pressures within chambers 55 and 59 are substantially equal at all times. Although other oxygen sensors may be used with the present invention, an oxygen sensor having the pressure equalization features of the oxygen sensor 52 in the embodiment of FIG. 3 is presently preferred. One oxygen sensor having such pressure equalization features and which has been found to be suitable for purposes of the present invention is the "Series. 6" zirconium oxide oxygen sensor manufactured by Sensors, Inc., Saline, Mich.

The microprocessor 62 receives signals from the various components of the metabolic gas monitoring apparatus as depicted by lines 81–84 and uses them to calculate the respiratory function. For example, microprocessor 62 receives data as to the carbon dioxide and oxygen concentrations sensed by carbon dioxide sensor 48 and oxygen sensor 52, respectively, through lines 83 and 84. Microprocessor 62 receives temperature data on line 82 from the temperature sensor 33 within mixing chamber 32, and receives flow rate data on line 81 from flow meter 36. Microprocessor 62 controls the switching mechanism 30, through line 80.

After comparing the relative concentrations of carbon dioxide and oxygen in the inspired gas and expired respiratory gas samples, microprocessor 62 calculates the metabolic rate of the patient and then outputs this information through lines 85 and 87 to the display unit 15 and printer 17. Microprocessor 62 may be any conventional microprocessing system; for example, the microprocessor made by Rockwell International of Anaheim, Calif., has been found to be suitable for purposes of the present invention.

Initially, carbon dioxide sensor 48 and oxygen sensor 52 must be calibrated. To accomplish this, the microprocessor 62 signals switching mechanism 30 which then passes the calibration gas from conduit 22 into conduit 42. The calibration gas flows through cooler 44, gas conduit 46, and into carbon dioxide sensor 48. The calibration gas then passes from carbon dioxide sensor 48 through gas conduit 50 and into oxygen sensor 52. The gas is then drawn by pump 56 through gas conduit 54 and 58 to the exhaust. The measured concentrations of oxygen and carbon dioxide are signaled to microprocessor 62 for calibration of the system.

In the calibration of sensor 48, generally two calibration gases are needed. Typically, a commercially available calibration gas containing 10% carbon dioxide, 21% oxygen, and 69% nitrogen is used to calibrate sensor 48, It will be appreciated, however, that other suitable calibration gases are also available. For example, a calibration gas containing 10% carbon dioxide, 15% oxygen, and 75% nitrogen may also be used. For the second calibration gas, typically ambient air is introduced from conduit 24 through the switching mechanism 30 to conduit 42 in much the same manner as with the first calibration gas. The ambient air provides a second calibration point for calibrating carbon dioxide sensor 48.

In the calibration of oxygen sensor 52, only one calibration gas, such as the calibration gas described above comprising 10% carbon dioxide, 21% oxygen, and 69% nitrogen, is needed where a zirconium oxide sensor is employed. Since the electric potential of the zirconium oxide oxygen sensor 52 decreases logarithmically with a decrease in oxygen concentration, and since the logarithmic response is stable over long periods of time, only one reference point and thus only one calibration gas is needed to calibrate the oxygen sensor 52.

After sensors 48 and 52 of apparatus 10 have been calibrated, microprocessor 62 signals switching mechanism 30 to allow a sample of inspired gas to flow through gas conduit 24 and into gas conduit 42. The inspired gas then passes through cooler 44, gas conduit 46, and into carbon dioxide sensor 48 which measures the amount of carbon dioxide in the sample. The inspired gas then passes through gas conduit 50 and into oxygen sensor 52 which measures the amount of oxygen in the inspired gas sample. Pump 56 removes the gaseous sample through conduits 54 and 58. Microprocessor 62 next operates switching mechanism 30 to allow expired respiratory gas to enter the apparatus 20 through gas conduit 40.

In this mode, the average metabolic rate over a short period of time will be measured. Expired gas from the patient first enters gas conduit 28 and flows into flow meter 36 where the expiration flow rate of the patient is measured and is signaled to the microprocessor 62 through line 81. Flow meter 36 may be, for example, a model 8311 pneumotachometer made by Hans Rudolph, Inc., of Kansas City, Mo. The gas then flows into mixing chamber 32 which has, for example, a chamber volume of 250 ml., so as to average several breaths expired by the patient. The temperature of the expired gas within mixing chamber 32 is measured by temperature sensor 33 and this temperature data is communicated to microprocessor 62 via line 82. The mixed respiratory gas exits mixing chamber 32 through gas conduit 38.

The expired respiratory sample enters conduit 40 and flows through switching mechanism 30 into gas conduit 42. From this point, the expired respiratory gas follows the same path as for the calibration gas and inspired gas, passing through cooler 44 and sensors 48 and 52 and exiting through the exhaust. Again, the carbon dioxide and oxygen concentrations in the expired gas sample are measured by sensors 48 and 52 and are compared with those for the inspired gas sample by microprocessor 62. Microprocessor 62 then calculates the metabolic rate and the results are displayed at display unit 15 and/or printed at printer 17.

In the breath-by-breath mode, only the concentration of carbon dioxide and oxygen in each breath are measured, and the metabolic rate is not calculated. Thus, after calibration as discussed above switching mechanism 30 allows entry of expired respiratory gas through gas conduit 26. The carbon dioxide and oxygen concentrations in each breath are measured by sensors 48 and 52, respectively, and the data is reported to microprocessor 62 and displayed at display unit 15 and/or printed at printer 17.

From the foregoing, it will be appreciated that the apparatus and method of the present invention provide a substantial advance in the state of the art by providing for accurate monitoring of respiratory gases in the case of newborn infants requiring mechanical ventilation. The apparatus and method of the present invention effectively isolates the respiratory gas from the main ventilation stream so that the respiratory gases can be accurately and effectively analyzed using state of the art electronics which are used to quickly provide data from which the necessary information can be derived concerning proper ventilator settings, metabolic rate, cardiovascular function and other important clinical data needed to properly care for the patient. The apparatus is also compact, and relatively inexpensive.

The invention may be embodied in other specific forms without departing from its spirit or essential characteristics, and the foregoing preferred embodiment is to be considered in all respects only as illustrative and not restrictive. The scope of the invention is therefore indicated by the appended claims and all changes which come within the meaning and range of equivalency of the claims are to be embraced within their scope.

What is claimed and desired to be secured by U.S. Letters Patent is:

1. In a system for mechanically ventilating a patient, an apparatus comprising:
    means for forming a first fluid flow circuit from which said patient is ventilated by a stream of oxygen enriched gas;
    means for forming a second fluid flow circuit connected to said first circuit, said second circuit comprising means for isolating respiratory gases expired by said patient from said first circuit, said second circuit further comprising an inlet end connected at a first point in said first circuit and an outlet end connected at a second point in said first circuit, the resistance to fluid flow from said inlet end to said outlet end of said second circuit being from about 10 to about 100 times greater than the resistance to fluid flow between said first and second points in said first circuit;
    a cooler capable of removing water vapor from said respiratory gases, said cooler comprising a first thermoelectric cooling block and a second insulating block mounted to said first block, a wick placed between said first and second blocks, said wick being capable of absorbing water, and a length of tubing placed between said blocks and in contact with said wick, said tubing consisting of hydrophilic material which allows for the passage of water through the walls of said tubing;
    means connected to said second circuit, for detecting the concentration of one or more gases contained in a gaseous sample flowing through said second circuit; and
    means for electronically processing information derived from said means for detecting the concentration of one or more said gases.

2. An apparatus as defined in claim 1 wherein said second circuit further comprises a flow meter and a mixing chamber connected in series between said inlet and outlet ends.

3. An apparatus as defined in claim 2 further comprising means connected to the outlet end of said mixing chamber for communicating to said detecting means a sample of the expired respiratory gases which have passed through said mixing chamber.

4. An apparatus as defined in claim 1 wherein said second circuit further comprises a two-way valve connected in series at said inlet end of said second circuit.

5. An apparatus as defined in claim 4 further comprising means connected at the inlet end of said valve for communicating to said detecting means a sample of the oxygen enriched gas inspired by said patient.

6. An apparatus as defined in claim 4 further comprising means connected at the outlet end of said valve for communicating to said detecting means a breath-by-breath sample of the respiratory gases expired by said patient.

7. In a system for mechanically ventilating a patient, an apparatus comprising:
    means for forming a first fluid flow circuit through which said patient is ventilated by a stream of oxygen enriched gas;
    means for forming a second fluid flow circuit, said second fluid flow circuit comprising an inlet end connected at a first point to said first circuit and an outlet end connected at a second point to said first circuit, said second circuit having a resistance to fluid flow from the inlet end to the outlet end thereof which is from about 10 to about 100 times greater than the resistance to fluid flow between said first and second points in said first circuit so as to prevent said oxygen enriched gas from flowing through said second circuit during inspiration by said patient, said second circuit further comprising valve means connected to said inlet end of said second circuit such that said patient may inspire through said valve means the oxygen enriched gas from said first circuit, and may thereafter expire respiratory gases through said valve means into said second circuit, said second circuit further comprising a flow meter and a mixing chamber connected in series between the inlet and outlet ends of said second circuit;
    means, connected to said second circuit, for detecting the concentration of one or more gases contained in a gaseous sample flowing through said second circuit;
    means for electronically processing information derived from said means for detecting the concentration of one or more said gases;
    a first fluid flow conduit having one end thereof connected at the outlet end of said mixing chamber and the other end thereof in fluid communication with said means for detecting the concentration of one or more said gases;
    a second fluid flow conduit having one end thereof connected to said second circuit between said valve means and said mixing chamber, said second fluid flow conduit having the other end thereof connected in fluid communication with said means for detecting the concentration of one or more said gases;
    a third fluid flow conduit having one end thereof connected at the inlet end of said valve means and having the other end thereof connected in fluid communication with said means for detecting the concentration of one or more said gases; and
    means for automatically selecting one of said first, second and third fluid flow conduits so as to place the selected conduit in fluid communication with said means for detecting the concentration of one or more said gases, said means for automatically selecting one of said conduits being electronically connected to and controlled by said means for electronically processing said information.

8. An apparatus as defined in claim 7 further comprising a first fluid flow conduit having one end thereof connected at the outlet end of said mixing chamber and the other end thereof in fluid communication with said means for detecting the concentration of one or more said gases.

9. An apparatus as defined in claim 8 further comprising a second fluid flow conduit having one end thereof connected to said second circuit between said valve means and said mixing chamber, said second fluid flow conduit having the other end thereof connected in fluid communication with said means for detecting the concentration of one or more said gases.

10. An apparatus as defined in claim 9 further comprising a third fluid flow conduit having one end thereof connected at the inlet end of said valve means and having the other end thereof connected in fluid communication with said means for detecting the concentration of one or more said gases.

11. An apparatus as defined in claim 10 further comprising means for automatically selecting one of said first, second and third fluid flow conduits so as to place the selected conduit in fluid communication with said means for detecting the concentration of one or more said gases, said means for automatically selecting one of said conduits being electronically connected to and controlled by said means for electronically processing said information.

12. An apparatus as defined in claim 7 further comprising a cooler connected in fluid communication with said second circuit, said cooler comprising means for removing water vapor from gases passing through said cooler.

13. An apparatus as defined in claim 12 wherein said cooler comprises a first thermoelectric cooling block and a second insulating block mounted to said first block, a wick placed between said first and second blocks, said wick being capable of absorbing water, and a length of tubing placed between said blocks and in contact with said wick, said tubing consisting of hydrophilic material which allows for the passage of water therethrough.

14. In a system for mechanically ventilating a patient, a method for monitoring the respiratory gases expired by said patient, said method comprising the steps of:
ventilating said patient with a stream of oxygen enriched gas provided through a first fluid flow circuit;
isolating the respiratory gases expired by said patient in a second fluid flow circuit connected in parallel at the inlet end thereof to said first circuit and connected at the outlet end thereof to said first fluid flow circuit at a point downstream from said inlet end connection;
structuring said first and second circuits such that the resistance to fluid flow within said second circuit is from about 10 to about 100 times greater than the resistance to fluid flow within said first circuit;
placing a length of hydrophilic tubing in contact with a thermoelectric block;
reducing the temperature of said thermoelectric block;
introducing said respiratory gases expired by said patient into said length of hydrophilic tubing such that said respiratory gases will be cooled as said gases flow through said hydrophilic tubing, whereby water vapor is condensed out of said respiratory gases and is allowed to pass through the walls of said hydrophilic tubing while said respiratory gases remain within said hydrophilic tubing;
placing an absorbent material in contact with at least a portion of the length of said hydrophilic tubing, such that said absorbent material will absorb and evaporate said water vapor which is passed through the walls of said hydrophilic tubing;
detecting the concentrations of one or more gases contained in said respiratory gases isolated in said second circuit; and
electronically processing information derived from the detected concentration of said gases.

15. A method as defined in claim 14 wherein said second fluid flow circuit further comprises a mixing chamber connected in series in said second circuit, and wherein said method comprises the step of detecting the concentration of one or more gases contained in said respiratory gases after said respiratory gases have passed through said mixing chamber.

16. A method as defined in claim 14 further comprising the step of detecting the concentration of one or more gases contained in the oxygen enriched gas inspired by said patient from said first fluid flow circuit.

17. A method as defined in claim 14 wherein said second fluid flow circuit further comprises valve means connected in series at the inlet end of said second circuit, and wherein said method further comprises the step of closing the inlet end of said valve means as said respiratory gases are expired by said patient so as to prevent said respiratory gases from mixing with said oxygen enriched gas from said first fluid flow circuit.

18. A method as defined in claim 14 further comprising the steps of:
placing a length of hydrophilic tubing in contact with a thermoelectric block;
reducing the temperature of said thermoelectric block;
introducing said respiratory gases expired by said patient into said length of hydrophilic tubing such that said respiratory gases will be cooled as said gases flow through said hydrophilic tubing, whereby water vapor is condensed out of said respiratory gases and is allowed to pass through the walls of said hydrophilic tubing while said respiratory gases remain within said hydrophilic tubing; and
placing an absorbent material in contact with at least a portion of the length of said hydrophilic tubing, such that said absorbent material will absorb and evaporate said water vapor which is passed through the walls of said hydrophilic tubing.

19. In a system for mechanically ventilating a patient, an apparatus for removing water vapor from respiratory gases expired by said patient and carried away in a respiratory gas conduit attached to said mechanically ventilating system, comprising:
a first thermoelectric cooling block and a second insulating block mounted to said first block, said first and second blocks having a chamber formed therebetween;
a length of hydrophilic tubing placed in said chamber between said first and second blocks, said tubing having an inlet end for introducing of a gaseous sample into said tubing and an outlet end through which said gaseous sample is removed after water vapor has been removed from said gaseous sample, said length of hydrophilic tubing being in contact along at least a portion of its length with said thermoelectric block such that said gaseous sample will be cooled as it travels from the inlet end of said tubing to the outlet end thereof, whereby water vapor will be condensed and will pass through said hydrophilic tubing; and
means for absorbing and evaporating the water vapor which has passed through said hydrophilic tubing.

20. An apparatus as defined in claim 19 wherein said means for absorbing and evaporating said water vapor comprises a thin sheet of material placed between said first and second blocks in contact with at least of a portion of the length of said hydrophilic tubing, at least a portion of said material extending beyond the periphery of said first and second blocks.

21. An apparatus as defined in claim 19 wherein said length of tubing is coiled in said chamber formed between said first and second blocks so as to form an effectively longer flow path through which said gaseous sample travels as it is cooled.

22. An apparatus as defined in claim 19 wherein said insulating block is transparent to permit visual inspection of said length of hydrophilic tubing situated between said first and second blocks.

23. A method of using a system for mechanically ventilating a patient and for removing water vapor from respiratory gases expired by said patient, said method comprising the steps of:
placing a length of hydrophilic tubing in contact with a thermoelectric block along at least a portion of the length of said hydrophilic tubing;
reducing the temperature of said thermoelectric block so as to cool the portion of said length of hydrophilic tubing in contact with said thermoelectric block;
introducing a gaseous sample into said length of hydrophilic tubing such that said gaseous sample will be cooled to permit condensation of water vapor as said gaseous sample travels from the inlet to the outlet end of said length of hydrophilic tubing;
whereby, said water vapor will pass through the walls of said hydrophilic tubing while said gaseous sample will remain within said hydrophilic tubing; and
placing an absorbent material in contact with at least a portion of said hydrophilic tubing such that said water vapor passed through the walls of said hydrophilic tubing will be absorbed and evaporated by said absorbent material.

24. In a system for mechanically ventilating a patient, an apparatus comprising:
means for forming a first fluid flow circuit from which said patient is ventilated by a stream of oxygen enriched gas;
means for forming a second fluid flow circuit connected to said first circuit, said second circuit comprising means for isolating respiratory gases expired by said patient from said first circuit;
a cooler in fluid communication with said second circuit, said cooler being capable of removing water vapor from said respiratory gases and said cooler comprising:
means for cooling said respiratory gases such that water vapor in said respiratory gases condenses comprising a first thermoelectric cooling block and a second insulating block mounted to said first block;
a length of tubing consisting of hydrophilic material which allows for the passage of water through the walls of said tubing, and through which said respiratory gases are passed as they are cooled by said cooler; and
means for removing water from said cooler comprising a wick capable of absorbing water, said hydrophilic tubing being placed between said blocks and in contact with said wick, said wick also being in contact with said hydrophilic tubing;
means, connected to said second circuit, for detecting the concentration of one or more gases contained in a gaseous sample flowing through said second circuit; and
means for electronically processing information derived from said means for detecting the concentration of one or more said gases.

25. An apparatus as defined in claim 24:
wherein said means for cooling said respiratory gases such that water vapor in said gases condenses comprises a first thermoelectric cooling block and a second insulating block mounted to said first block; and
wherein said means for removing water from said cooler comprises a wick capable of absorbing water, said hydrophilic tubing being placed between said blocks and in contact with said wick.

26. In a system for mechanically ventilating a patient, an apparatus comprising:
means for forming a first fluid flow circuit through which said patient is ventilated by a stream of oxygen enriched gas;
means for forming a second fluid flow circuit, said second fluid flow circuit comprising an inlet end connected at a first point to said first circuit and an outlet end connected at a second point to said first circuit, said second circuit having a resistance to fluid flow from the inlet end to the outlet end thereof which is greater than the resistance to fluid flow between said first and second points in said first circuit so as to prevent said oxygen enriched gas from flowing through said second circuit during inspiration by said patient, and said second circuit further comprising valve means connected at said inlet end of said second circuit such that said patient may inspire through said valve means the oxygen enriched gas from said first circuit, and may thereafter expire respiratory gases through said valve means into said second circuit;
a cooler connected in fluid communication with said second circuit for removing water vapor from gases passing through said cooler, said cooler comprising:
a first thermoelectric cooling block and a second insulating block mounted to said first block;
a wick placed between said first and second blocks, said wick being capable of absorbing water; and
a length of tubing placed between said blocks and in contact with said wick, said tubing consisting of hydrophilic material which allows for the passage of water through the walls of said tubing;
means, connected to said second circuit, for detecting the concentration of one or more gases contained in a gaseous sample flowing through said second circuit; and
means for electronically processing information derived from said means for detecting the concentration of one or more said gases.

27. A method of using a system for mechanically ventilating a patient and for monitoring the respiratory gases expired by said patient, said method comprising the steps of:
ventilating said patient with a stream of oxygen enriched gas provided through a first fluid flow circuit;
isolating the respiratory gases expired by said patient in a second fluid flow circuit connected to said first circuit;
placing a length of hydrophilic tubing in contact with a thermoelectric block;
reducing the temperature of said thermoelectric block;
introducing said respiratory gases expired by said patient into said length of hydrophilic tubing such that said respiratory gases will be cooled as said gases flow through said hydrophilic tubing, whereby water vapor is condensed out of said respiratory gases and is allowed to pass through the walls of said hydrophilic tubing while said respiratory gases remain within said hydrophilic tubing; placing an absorbent material in contact with at least a portion of the length of said hydrophilic tubing, such that said absorbent material will absorb and evaporate said water vapor which is passed through the walls of said hydrophilic tubing;

detecting the concentrations of one or more gases contained in said respiratory gases isolated in said second circuit; and electronically processing information derived from the detected concentrations of said gases.

* * * * *